US00PP17063P3

(12) United States Plant Patent
Cummins et al.

(10) Patent No.: US PP17,063 P3
(45) Date of Patent: Aug. 29, 2006

(54) APPLE TREE ROOTSTOCK NAMED 'G.935'

(50) Latin Name: *Malus domestica×Malus robusta hybrid*
Varietal Denomination: G.935

(75) Inventors: James Cummins, Geneva, NY (US); Herbert Aldwinckle, Geneva, NY (US); Terence Robinson, Geneva, NY (US); Gennaro Fazio, Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/047,370

(22) Filed: Jan. 31, 2005

(65) Prior Publication Data

US 2006/0174386 P1 Aug. 3, 2006

(51) Int. Cl.
*A01H 5/00* (2006.01)

(52) U.S. Cl. ..... Plt./174

(58) Field of Classification Search ..... Plt./174
See application file for complete search history.

*Primary Examiner*—Anne Marie Grunberg
*Assistant Examiner*—Annette H Para
(74) *Attorney, Agent, or Firm*—Jondle & Associates P.C.

(57) ABSTRACT

A new and distinct variety of apple tree rootstock *Malus domestica×Malus robusta* hybrid 'G.935' is described herein. The new variety is a dwarfing rootstock that is resistant to fire blight (*Erwinia amylovora*) and crown rot (*Phytophthora cactorum*). The 'G.935' rootstock is useful in that it can be propagated clonally and used as a rootstock or root system for apple trees as well as for interstems of apple trees.

5 Drawing Sheets

Genus and species: *Malus domestica×Malus robusta* hybrid.
Variety denomination: 'G.935'.

BACKGROUND AND SUMMARY OF THE INVENTION

The invention described here is a new variety of apple tree rootstock, *Malus domestica×Malus robusta* hybrid, hereinafter referred to as 'G.935'. 'G.935' originated from a planned cross in 1976 in Geneva, N.Y. The new variety is a dwarfing rootstock that is resistant to fire blight and crown rot. It is precocious and highly productive, and can be used as a rootstock and for interstems of apple trees.

In the spring of 1976, pollen from a *Malus robusta* 'Robusta 5' apple tree was applied to emasculated flowers of a *Malus domestica* 'Ottawa 3' apple tree at the New York State Agricultural Experiment Station ("NYSAES"), Cornell University, Geneva, N.Y. In the fall of 1976, approximately 500 seeds resulting from this pollination were extracted from mature fruit derived from this cross. In the winter of 1976–77, the seeds were stratified and planted in large flats under conditions effective to germinate seeds and obtain seedlings. When germinated seedlings were about 2.5 cm tall they were inoculated with a mixture of isolates of the fungus *Phytophthora cactorum* (the causal agent of crown and root rots). The flats were flooded to mid-hypocotyl level and kept at 23° C. for one week. Surviving seedlings were transplanted into individual pots.

In the summer of 1976, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #935 was one of the survivors of this battery of inoculations from the same cross. All the surviving plants were transplanted to the Loomis field (NYSAES, Cornell University, Geneva, N.Y.) in the fall of 1977 and allowed to grow side shoots for propagation/evaluation. In 1980, 'G.935' was evaluated for rooting ability, lack of spine production, and low root brittleness in a layering bed (stool bed). In 1983, 4 finished trees with 'G.935' rootstock were planted in a first test orchard on the Loomis farm (NYSAES, Cornell University, Geneva, N.Y.) with *Malus domestica* cv. 'Northern Spy' grafted onto this rootstock as the scion cultivar. This rootstock performed well (top 20% of many rootstocks tested) in these first test trials and during 1990–1993 more material was propagated by stool bed and nursery to be entered into new trials at the Hansen Farm (NYSAES, Cornell University, Geneva, N.Y.) with *Malus domestica* cv. Empire as the scion cultivar. The 'G.935' rootstock performed well with all the scion cultivars that were tested. In August of 2002, several rootstock liners of 'G.935' were budded with 15 different scion cultivars to test graft union compatibility—the test results showed that 'G.935' was compatible with all the cultivars tested. In summer 2002, 40 rootstock liners were inoculated with four different strains of fire blight (ten liners per strain) in the Plant Genetic Resources Unit greenhouse (NYSAES, Cornell University, Geneva, N.Y.) of the U.S. Department of Agriculture Agricultural Research Service. As a result, the apple rootstock 'G.935' was classified as immune to two of the strains tested and moderately resistant to the other two strains of fire blight.

Asexual reproduction of the 'G.935' apple rootstock has been achieved using the traditional method of clonally propagating apple rootstocks. In particular, the original seedling of the 'G.935' apple rootstock was planted in the Loomis field (NYSAES, Cornell University, Geneva, N.Y.) and allowed to develop into a "mother plant." The 'G.935' mother plant was then used to obtain rooted liners using conventional layering procedures. The resulting liners were then planted in a row to generate a layering stool bed (also referred to as the "mother stool bed"). The living tissues (i.e. leaves, stems, roots, buds, and spines) of the mother stool bed were observed to be identical to secondary and tertiary stool bed plants. In addition to conventional layering, the 'G.935' apple rootstock variety has been asexually reproduced by root cuttings, by budding and grafting onto seedling and clonal rootstocks, and by tissue culture. Observations of trees from these propagations indicate that all trees have proven true to type and identical in all appearances to the original tree.

COMPARISON WITH PARENTAL AND KNOWN CULTIVARS

The seed parent *Malus domestica* 'Ottawa 3' is a dwarfing rootstock, i.e., trees grown on this rootstock are 30 to 35 percent the size of a standard self-rooted seedling tree. 'Ottawa 3' is known to induce good precocity to the scion (i.e., the ability to induce early reproductive development in the scion) and has high yield efficiency. 'Ottawa 3' plants produce no spines, are fairly well anchored, are a very cold hardy rootstock and have resistance to crown and root rot caused by *Phytophthora cactorum*. However, 'Ottawa 3' is susceptible to the woolly apple aphid (*Eriosoma lanigerum*) and to fire blight (*Erwinia amylovora*).

The pollen parent *Malus robusta* 'Robusta 5' is a non-dwarfing rootstock, i.e. trees on this rootstock are the same size as a standard self-rooted tree. 'Robusta 5' does not induce precocity to the scion and is not highly yield efficient. Juvenile plants of 'Robusta 5' produce many spines. 'Robusta 5' breaks buds very early in the spring and is winter hardy. It is resistant to powdery mildew (*Podosphaera leucotricha*) and fire blight, and is immune to the woolly apple aphid. Further, 'Robusta 5' has shown tolerance to the specific replant disease complex.

The 'G.935' apple rootstock of the present invention has a combination of qualities that distinguishes it from its parental plants (i.e., 'Ottawa 3' and 'Robusta 5'). For example, although 'G.935' has dwarfing properties derived from 'Ottawa 3', it is different from its dwarfing parent (i.e., 'Ottawa 3') because it produces a tree that is 45 to 55 percent of the size of a standard self-rooted seedling tree. Thus 'G.935' belongs to a different dwarfing vigor class than its 'Ottawa 3' parent. In particular, 'G.935' has dwarfing characteristics that are similar to the industry standard of *Malus domestica* 'Malling 7'. 'G.935' shares similarities with 'Ottawa 3' in that they both induce precocity to the scion, are highly yield efficient and winter hardy.

With regard to its 'Robusta 5' parent, 'G.935' is distinguishable in that it is a dwarfing rootstock and is highly yield efficient, while 'Robusta 5' is not. However, like 'Robusta 5', 'G.935' is resistant to fire blight and powdery mildew. In addition, 'G.935' has been shown to have some tolerance to the replant disease complex. Unlike its 'Robusta 5' parent, 'G.935' is susceptible to the woolly apple aphid (*Eriosoma lanigerum*).

As discussed above, 'G.935' is most similar to 'Malling 7' in terms of dwarfing class. However, 'G.935' is more precocious and yield efficient than 'Malling 7'. 'G.935' is resistant to fire blight whereas 'Malling 7' and other rootstocks in its market class are not.

BRIEF SUMMARY OF THE INVENTION

The present invention relates to a new and distinct variety of apple tree rootstock named 'G.935'. The 'G.935' apple tree rootstock is a dwarfing rootstock that is resistant to fire blight (*Erwinia amylovora*) and crown rot (*Phytophthora cactorum*). The 'G.935' rootstock is useful in that it can be propagated clonally and used as a rootstock or root system for apple trees as well as for interstems of apple trees. While 'G.935' rootstock is a hybrid from a cross between 'Ottawa 3' and 'Robusta 5', it is distinct from its parent cultivars in terms of dwarfing. The apple tree rootstock 'G.935' is less dwarfing than 'Ottawa 3' and more dwarfing than the non-dwarfing parent 'Robusta 5'. Unlike 'Ottawa 3', 'G.935' is resistant to fire blight. Although 'G.935' is in the same dwarfing market class as 'Malling 7', it is distinguishable from 'Malling 7' because 'G.935' is resistant to fire blight and precocious whereas 'Malling 7' is susceptible and non-precocious.

DETAILED BOTANICAL DESCRIPTION OF THE INVENTION

Figure 1:
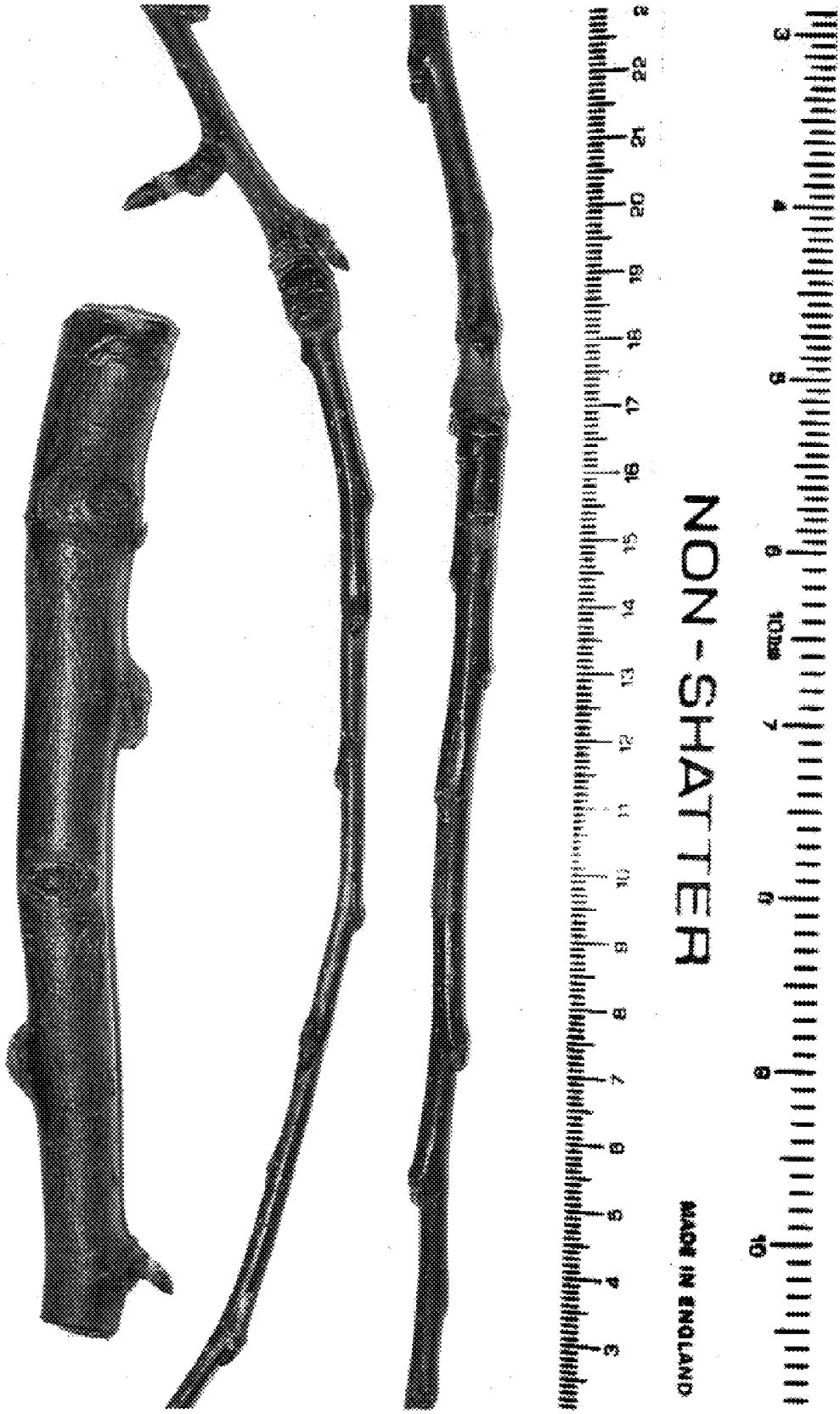
FIG. 1 shows a dormant shoot (including buds and bark).
Figure 2:
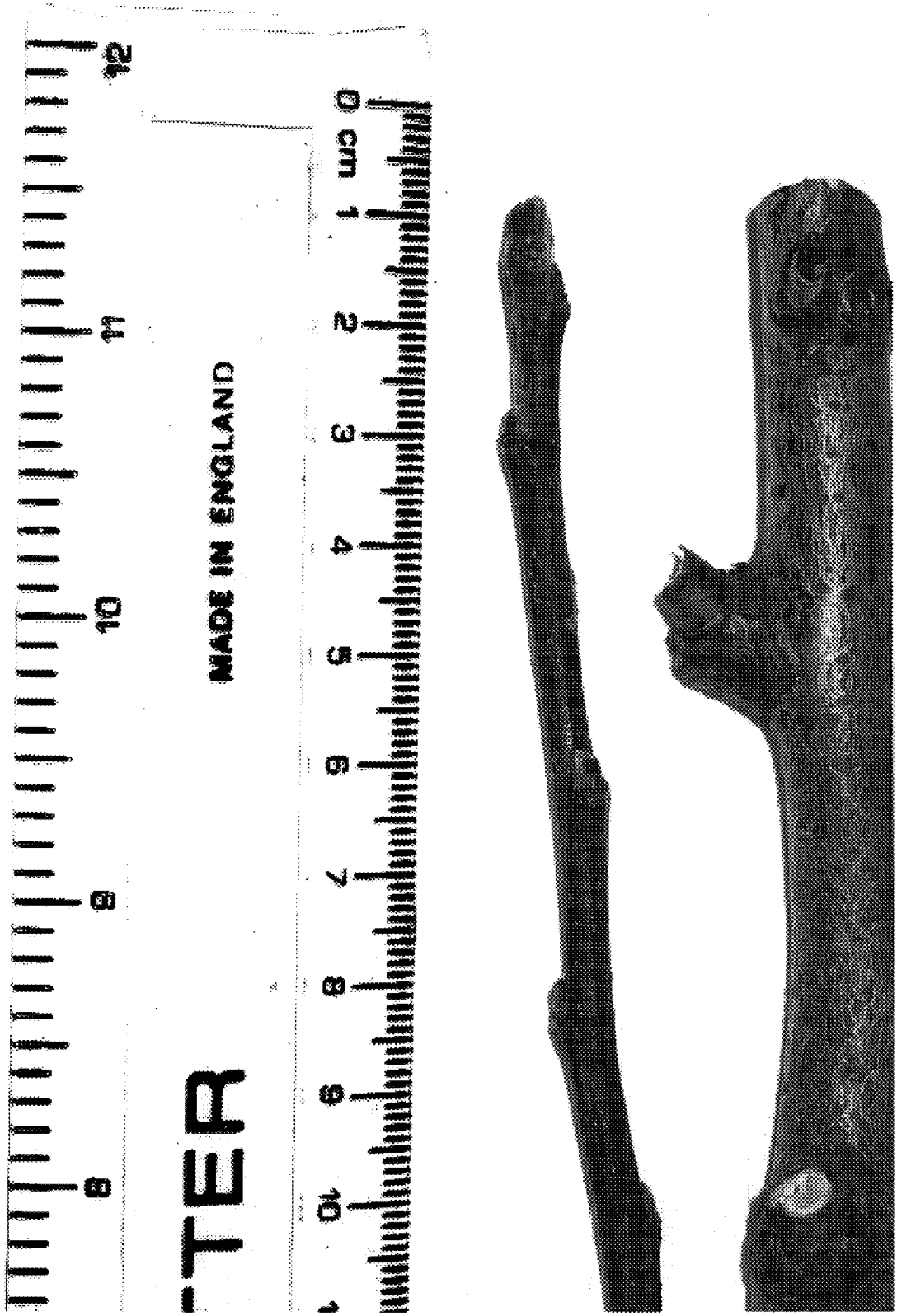
FIG. 2 shows a close-up view of a dormant shoot (including buds and bark).
Figure 3:
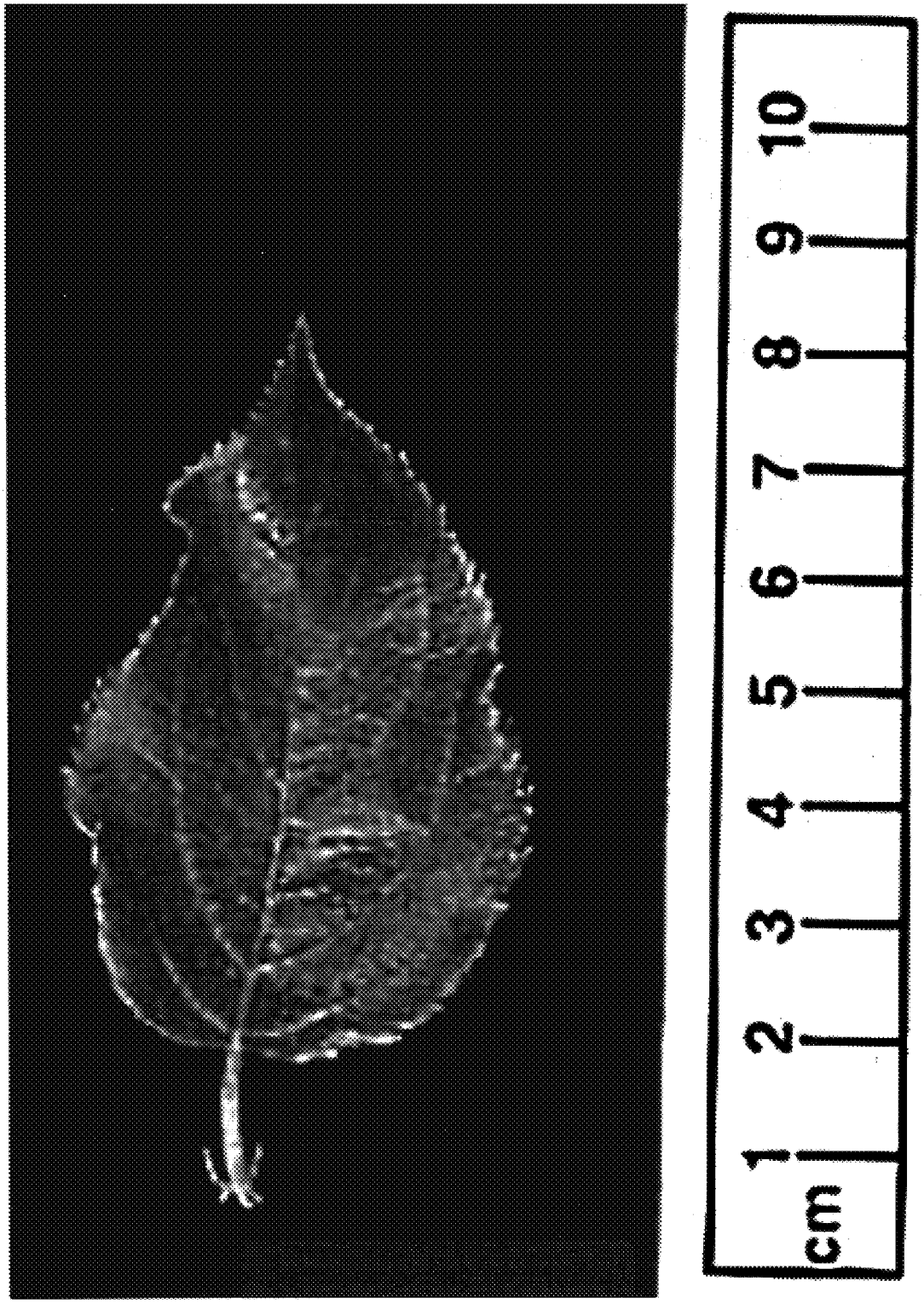
FIG. 3 shows the adaxial (upper) lamina surface of a mature leaf.
Figure 4:
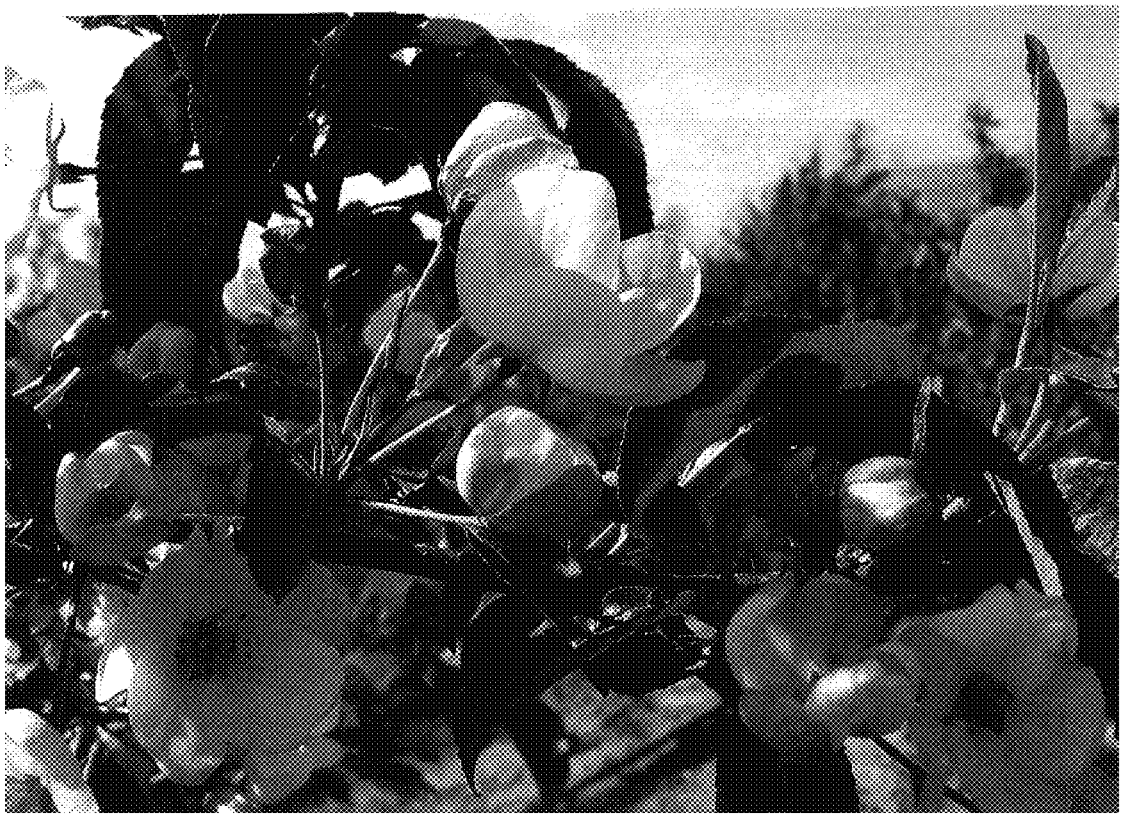
FIG. 4 shows leaves and flowers.
Figure 5:
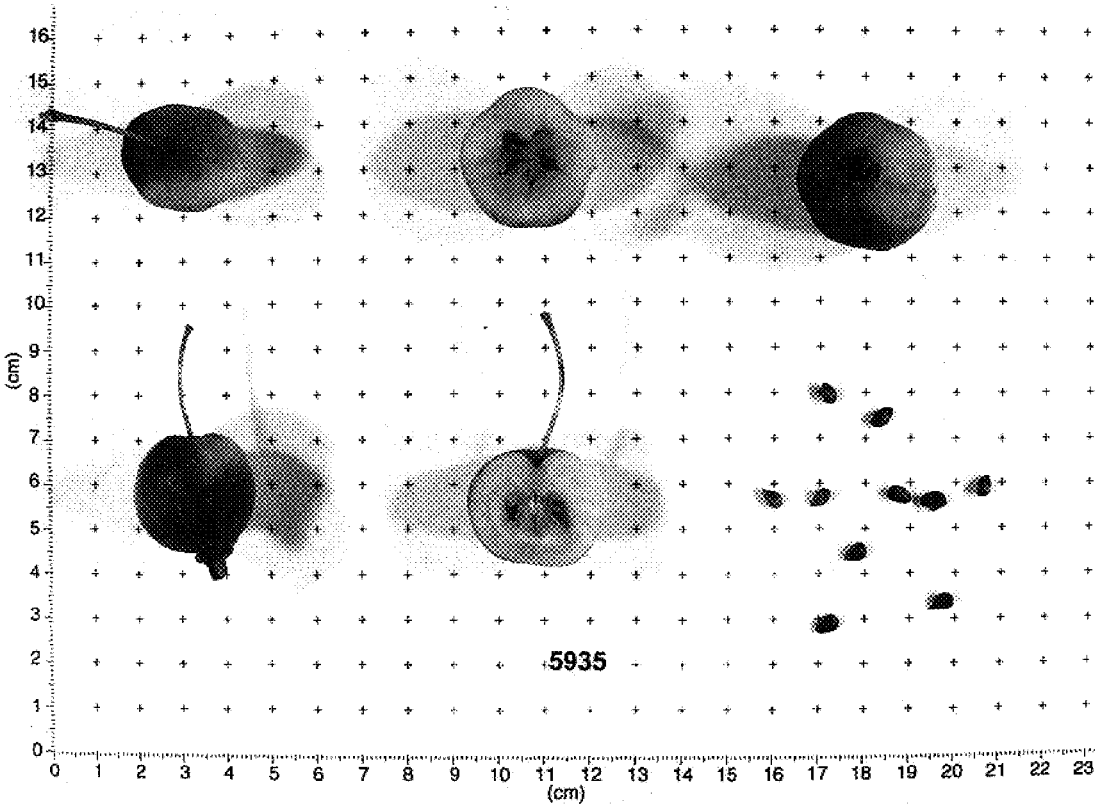
FIG. 5 shows the mature fruit.

The following description of apple tree rootstock 'G.935' contains references to color names taken from The Royal Horticultural Society Colour Chart (R.H.S.), 2001 edition. Botanical descriptions follow the Manual of Cultivated Plants (Bailey, 1949).

Tree:

*Habit.*—A self-rooted tree of 'G.935' is a small shrub typically standing about 1.5–2 meters tall by about 2 meters wide when 7 years old. There is no single dominant trunk. Instead there are few shoots arising from the crown. Very few suckers (i.e., new shoots emerging from below ground) are produced. Liners planted in the nursery stop apical growth mid season. The apical bud in these plants is pubescent Greyed-Green (RHS 191D).

*Productivity.*—In an intermediate trial performed at the NYSAES (Cornell University, Geneva, N.Y.), the 'G.935' rootstock received the cultivar 'Empire' (*Malus domestica*) as the scion and was compared to the *Malus domestica* check rootstocks M.9 EMLA, M.26 and M.7. 'G.935' was shown to have statistically higher ($p \leqq 0.05$) yield efficiency (kg yield/$cm^2$ trunk cross sectional area) than all the check rootstocks.

*Precocity.*—Scion cultivars budded on 'G.935' exhibit the same precocity as those budded on M.9.

*Fertility* (*fecundity*).—The 'G.935' plant produces flowers and fruits regularly.

Dormant shoots (buds and bark):

*Dormant mature shoots.*—Color: Greyed-Red (RHS 178A) where exposed to full sunlight grading to Greyed-Orange (RHS 173B) with diminished light exposure. Texture: Very light pubescence which gradually disappears in older tissues. Size: 30–60 cm long; may have some spines.

*Axillary buds.*—Size: 2–3 mm long and 3 mm wide with little pubescence. Shape: Obtuse, sessile, somewhat appressed and flattened. Texture: Some pubescence.

*Bark on three-year-old shoots.*—Color: Greyed-Green (RHS 197A). Lenticels: Color: Greyed-Orange (RHS 163B). Size: 0.3–0.4 mm in diameter. Quantity: 1–2 lenticels per $cm^2$.

Leaves:

*Mature leaves.*—Leaf arrangement: Alternate. Shape: Simple, recurved, oblong-ovate. Size: Length: 85 mm. Width: 50 mm at the widest point. Laminae: Somewhat wavy. Apex: Acuminate. Base: Nearly symmetrical rounded. Margin: Acutely serrated, with about 5 serrations per cm. Upper surface: Color: Green (RHS 126B). Texture: Glabrous and translucent. Lower surface: Color: Green (RHS 146C). Texture: Somewhat pubescent. Venation: Netted. Leaf poise: 15°–25° from the shoot, depending on shoot orientation. Stipules: Length: 8 mm. Width: 2 mm. Petioles: Diameter: 2 mm. Color: Gradation of Green (RHS 140A) to Greyed-Red (RHS 179A) depending on low or high exposure to light.

Flowers:

*Habit.*—Flowers borne on spurs, shoot terminals, and from lateral buds on growth from previous season.

*Flower diameter.*—40 mm.

*Fragrance.*—None.

*Buds.*—Location: Located on spurs and terminals; are mixed, typically producing a truss of 5 to 6 flowers and one bourse shoot. Shape: Lateral buds are obtuse, sessile and somewhat appressed. Size: Length: 4 mm. Width: 3 mm. Habit: Buds near the base of the shoot of the previous season usually produce 3 to 5 flowers and a single short shoot; mid-shoot buds may have 2–4 flowers; and more distal buds are usually vegetative.

*Petals.*—Size: Length: 25 mm. Width: 18 mm. Shape: Spatulate. Apex: Obtuse. Margin: Smooth. Texture: Smooth. Color: Closed petals: Red (RHS 54A). Open petals: White (RHS 155D) with Red (RHS 54A) striations in some of the petals.

*Reproductive organs.*—Pistils: Length: 6 mm. Color: Yellow-white (RHS 145B). Stamens: Length: 4 mm. Color: White (RHS 155D). Anther color: Yellow-Brown (RHS 167D).

Fruit:

*Mature fruit.*—Size: Height: 30–35 mm. Diameter: 30–35 mm. Shape: Obloid. Color: Partial Yellow-Orange skin (RHS 22A) with Red (RHS 46C) blush overtones depending on the exposure to the sun. Sepals: Persisting on a very protruding calyx. Flesh: Taste: Astringent (not meant for consumption). Color: Yellow-Orange (RHS 17C). Seed: Color: Greyed-Red (RHS 179A), translucent. Shape: Tear drop shape. Size: Length: 50–60 mm. Diameter: 25–35 mm at the widest point. Number: Generally five seed per fruit. The mean size of calyx under the fruit: 13.8 mm. Aperture eye: closed.

Disease resistance: As described above, the 'G.935' rootstock of the present invention exhibits resistance to fire blight. The percent lesion measured after inoculation of potted liners in the greenhouse using four different strains of *E. amylovora* was negligible for two of the strains and moderate for the other two, indicating a specific resistance to the bacterium. The 'G.935' rootstock, having survived the inoculation with crown and root rot, is also considered resistant to crown and root rots caused by *Phytophthora cactorum.*

What is claimed is:

1. A new and distinct variety of apple tree named 'G.935' herein described and illustrated.

* * * * *

UNITED STATES PATENT AND TRADEMARK OFFICE

CERTIFICATE OF CORRECTION

PATENT NO. : PP 17,063 P3
APPLICATION NO. : 11/047370
DATED : August 29, 2006
INVENTOR(S) : James Cummins et al.

It is certified that error appears in the above-identified patent and that said Letters Patent is hereby corrected as shown below:

In column 1 line 1: please insert as the first paragraph the following statement which should read:

--Statement Regarding Federally Sponsored Research and Funding: This invention was made with U.S. Government support under Contract No. 58-3K95-8-585 awarded by CRADA and associated with CRIS 1908-21000-007-10T, 58-3K95-M-1031 awarded by CRADA and associated with CRIS 1910-21000-022, 58-1907-7-039 a Specific Cooperative Agreement with Cornell University and 1910-21000-022 associated with CRIS, a USDA unit. The government has certain rights in this invention--

Signed and Sealed this

Twenty-ninth Day of April, 2008

JON W. DUDAS
*Director of the United States Patent and Trademark Office*